United States Patent [19]
Einarsson

[11] Patent Number: 5,714,477
[45] Date of Patent: Feb. 3, 1998

[54] PHARMACEUTICAL COMPOSITION CONTAINING HEPARIN, HEPARIN FRAGMENTS OR THEIR DERIVATIVES IN COMBINATION WITH GLYCEROL ESTERS

[75] Inventor: Monica Einarsson, Upsala, Sweden

[73] Assignee: Pharmacia & Upjohn Aktiebolag, Stockholm, Sweden

[21] Appl. No.: 569,087

[22] PCT Filed: Jun. 16, 1994

[86] PCT No.: PCT/SE94/00595

§ 371 Date: Dec. 4, 1995

§ 102(e) Date: Dec. 4, 1995

[87] PCT Pub. No.: WO95/00152

PCT Pub. Date: Jan. 5, 1995

[30] Foreign Application Priority Data

Jun. 18, 1993 [SE] Sweden ................................. 9302135

[51] Int. Cl.⁶ ........................ A61K 31/725; A61K 47/14
[52] U.S. Cl. ........................... 514/56; 514/786; 536/21
[58] Field of Search ..................... 514/56, 786; 536/21

[56] References Cited

U.S. PATENT DOCUMENTS

| | | |
|---|---|---|
| 3,510,561 | 5/1970 | Koh ............................................. 424/183 |
| 4,156,719 | 5/1979 | Sezaki et al. ............................... 424/118 |
| 4,434,159 | 2/1984 | Sekine et al. ............................... 424/178 |
| 4,656,161 | 4/1987 | Herr ............................................ 514/56 |

FOREIGN PATENT DOCUMENTS

| | | |
|---|---|---|
| 19920/88 | 12/1988 | Australia . |
| 0 130 555 A2 | 1/1985 | European Pat. Off. . |
| 0 331 948 A2 | 9/1989 | European Pat. Off. . |
| 0 014 184 B2 | 10/1989 | European Pat. Off. . |

OTHER PUBLICATIONS

Taniguchi K., Muranishi S., Sezaki H. Int. J. Pharm. 4, pp. 219–228, 1980.

Muranishi, S. Modification of Intestinal Absorption of Drugs by Lipoidal Adjuvants. *Pharmaceutical Research* 1985, pp. 108–118.

*Primary Examiner*—C. Warren Ivy
*Assistant Examiner*—Evelyn Huang
*Attorney, Agent, or Firm*—Pollack, Vande Sande & Priddy

[57] ABSTRACT

The present invention relates to pharmaceutical compositions containing heparin or heparin fragments or their derivatives in combination with one or more glycerol esters of at least one fatty acid as single absorption enhancer. The compositions are useful for oral administration, for administration through mucous membranes or for transdermal administration. The compositions will when necessary contain further physiologically acceptable additives, such as diluents and/or carriers, suitable for the adaptation to oral, buccal, rectal, sublingual, nasal, subcutaneous or transdermal administration. The composition according to the invention provide excellent absorption and bioavailability without employing additional enhancers or promoters.

20 Claims, No Drawings

PHARMACEUTICAL COMPOSITION CONTAINING HEPARIN, HEPARIN FRAGMENTS OR THEIR DERIVATIVES IN COMBINATION WITH GLYCEROL ESTERS

INTRODUCTION

This application is the national phase of PCT/SE94/00595, filed Jun. 16, 1994.

The present invention relates to pharmaceutical compositions containing heparin or heparin fragments or their derivatives in combination with one or more glycerol esters of at least one fatty add as single absorption enhancer. The compositions are useful for oral administration, for administration through mucous membranes or for transdermal administration. The compositions will when necessary contain further physiologically acceptable additives, such as diluents and/or carriers, suitable for the adaptation to oral, buccal, rectal, sublingual, nasal, subcutaneous or transdermal administration. The compositions according to the invention provides excellent absorption and bioavailability without employing additional enhancers or promoters.

BACKGROUND OF THE INVENTION

Heparin is a sulphate-containing polysaccharide widely used as an anti-coagulant, which originates from the intestinal mucosa of swine or lungs from cattles. It has been used for decades for the treatment and prevention of thrombosis. In recent years several new generations of heparin derivatives and fragments with more efficient and specific activity have been developed and marketed. Such low molecular fragments of heparin are disclosed e.g. in EP-A-0 014 184. The product, known as Fragmin®, is marketed by Pharmacia AB of Stockholm, Sweden.

It has been a considerable problem to find alternative administration routes to injections for all heparins and their fragments due to their poor absorbability, for example when administered orally or rectally. A safe and efficient alternative to injections is therefore demanded for increasing the convenience for patients subjected to long-term treatment with heparins or heparin fragments.

There are several disclosures of pharmaceutical systems for enhancing the penetration of heparins or low molecular weight derivatives thereof through body membranes. Different rectal or enteral compositions are described in the patent specifications U.S. Pat. No. 4,156,719, DE-A-3 331 009 and EP-A-0 037 943. In these disclosures the bioabsorption is enhanced by means of various surface active agents or by carboxylic adds such as salicylic acid and glutamic acid. Compositions containing sulfones and fatty alcohols for oral, buccal and sublingual administration of heparin are described in U.S. Pat. No. 3,510,561. WO-A-88/10117 relates to an oral heparin composition containing a monosaccharide and a salt of a metallic cation. EP-A-0 130 555 discloses pharmaceuticals containing heparins and non-ionic tensides with improved permeability in the mouth and the nose.

However, none of these disclosed compositions have successfully led to products which substitute parenteral administration of heparins or heparin fragments.

It is the object of the present invention to provide new compositions containing therapeutically effective amounts of heparin, heparin fragments or their derivatives, which have a bioavailability high enough to result in clinically relevant plasma levels, when administered orally or through mucous membranes or through the skin, comparable to those obtained from a subcutaneous or intramuscular injection. According to the present invention such compositions are conceivable by using heparin in combination with one or several glycerol esters of fatty adds in a pharmaceutical composition. Medium chain glycerides have previously been used as absorption enhancers both in rectal and topical compositions, but only successfully when smaller molecules and certain polypeptides such as calcitonin and insulin are used in the system, and in most applications together with additional enhancing vehicles, such as surface active agents. There are currently no successful compositions in terms of improved biological absorption with larger therapeutically useful hydrophilic polysaccharides (such as heparins and their fragments) with glycerides of fatty adds as absorption enhancing components.

DESCRIPTION OF THE INVENTION

The invention is generally related to a composition of a therapeutically effective amount of a heparin and/or heparin fragments and/or derivatives thereof and at least one glycerol ester of one or several fatty acids, a method for the manufacture of such a composition, the use of the composition for the manufacture of medical preparations and the use of glycerol esters of one or several fatty acids for enhancing the absorption of heparins through body membranes.

According to this invention the expression "a heparin" or "heparins" denotes any fraction or class of heparin from natural, biosynthetic or genetically engineered source, as well as any derivative thereof e.g. heparin esters. A fragment of heparin denotes any low molecular weight fragment of heparin or their derivatives having heparin activity including chemically modified, biosynthetic, semi-synthetic or synthetic heparin-like oligosaccharides. Suitably, the low molecular weight heparin fragments and/or their derivatives, have a molecular mass in the range of from about 1000 to 10000 Dalton.

A heparin fragment preferred according to the present invention is Fragmin®, which is, as mentioned above, disclosed in EP-A-0 014 184. The Fragmin® may be in the form of a solution or a suspension when added to or mixed with the other components of the composition. It can also be admixed as a powder or in a solution with an essentially water-flee lipid matrix consisting of the mentioned glycerides. Fragmin® is very readily soluble in water and such aqueous compositions are considered to have excellent stability. The solubility and stability of Fragmin® facilitates the adaption of the composition to a suitable administration form.

The glycerol esters of fatty acids according to the present invention are mono; di- or triglycerides or any mixtures thereof, of at least one fatty acid. The fatty acid residues can be the same or vary on the di- and tri-glyceride molecules. For a mixed population of mono-, di- and triglycerides the acyl groups or fatty acid residues can be the same or different in each category of molecule. Suitably, the acyl groups are carefully defined, preferably with a chain length of between 6 and 18 carbon atoms. The choice of relative composition of such mono-, di- or triglycerides in a composition according to the invention will depend on the actual administration route. Furthermore, the choice of the relative composition of such mono-, di- or triglycerides may be used as a device to control absorption rate and/or the release rate of the heparins, as the glycerides can differ both in chain length, in polarity, in the degree of unsaturation and in other physical properties such as melting point and viscosity.

Another suitable way to control the absorption and/or release rate of the heparins or their fragments is to vary the chain lengths of the acyl groups between 6 and 18 carbon atoms.

The properties of the composition containing heparins and glyceride esters of fatty acids will thus be influenced by the polarity, the chain lengths, the relative amounts of the constituents and the number of unsaturated bonds in the acyl groups of the glycerides.

Anyone skilled in the art will readily find suitable components for adapting the composition to an advantageous delivery system for therapeutically effective amounts of heparins, by varying the lipid constituents, for example by varying the choice of lipid start material, thereby obtaining compositions with different viscosity and absorption enhancing capacity.

A composition which is preferred according to the present invention will contain monoglycerides with defined acyl groups within the range of 6 to 18 carbon atoms. Suitable monoglycerides will essentially consist of a mixture of 8:0 caprylate and 10:0 caprate. Such compositions are very flexible in that they may easily be adapted to a variety of preparations fitting each desired administration route by adding suitable excipients.

Tests with heparin compositions containing triglycerides, also show improved absorption performance. The use of triglycerides is advantageous, since normally triglycerides are cheaper than both mono- and diglycerides. However, the concentration required to obtain enhanced absorption while at the same time avoiding a toxic effect may be higher with triglycerides than with mono- and/or diglycerides.

The preparation of the compositions according to the present invention can be performed in different manners, which are chosen with respect to the intended administration route. For example, when Fragmin® is to be mixed to a homogenous composition with the lipid component or components, it can be present as a powder, which is dispersed in the lipids, as solution with an excess amount of water to be admixed with the lipids or as solution which after mixing with the lipids provides an essentially water-free matrix composition. The flexibility and stability of Fragmin® makes it easy to adapt for any desired composition, such as a solution, a suspension or any semi-solid, viscous or solid matrix that is required for a specific administration form and for the specific quality of the glyceride component, for example in terms of viscosity and absorption enhancing properties.

Preparations can be adapted for rectal use in the form of foams, clysmas, capsules and suppositories or different preparations specially manufactured for oral, buccal, sublingual, nasal, transdermal and subcutaneous administration or for administration through mucous membranes in general. The inventive compositions containing heparins, their fragments or derivatives and glycerol esters of fatty acids are also suitable for the manufacture of a depot preparation for obtaining controlled release for e.g. subcutaneous administration or for controlled oral release by applying enclosing barrier membranes to the oral dosage forms. Another suitable preparation according to the invention are buccal dosage forms where the inventive composition is applied to a porous polymeric matrice or enclosed within an envelope optionally with mucoadhesive properties. The mentioned preparations are useful for treating and/or preventing a wide variety of pathological processes commonly associated with heparin therapy such as thromboembolic diseases, preinfarctional angina, coronary heart diseases, inflammatory diseases, thrombophlebitis, autoimmune diseases, arteriosclerosis or for treatment of methasthasis or angiogenesis related diseases. Every adaptation in terms of finding the appropriate excipients or vehicles for the compositions for the above-mentioned administration routes for treatments associated with heparins or their fragments will be obvious to persons skilled in this art.

The total dosage of the heparins or heparin fragments in the above-mentioned administration forms can thus be very high and is limited only by the bioavailability and by that which is therapeutically or clinically appropriate to administer and well tolerated. Examples of clinical doses of Fragmin® are 120 IU per kg body weight twice daily for deep venous thrombosis and for thrombosis prophylaxis 2500 IU per day (for low risk patients) or 5000 IU per day (for high risk patients). For example, the relative amount of Fragmin® to the lipids containing glycerol esters of fatty acids can be in the range of preferably 1–200% (w/w). However, a higher amount of either Fragmin® or lipids are conceivable within the context of the invention, if it is clinically suitable. If the amount of lipids will be too low in a composition the enhanced absorption effect will be reduced, which may be compensated by an increased amount of Fragmin, in order to obtain the same serum levels after administration or vice versa. This broad concentration range, which makes it possible to have Fragmin® to lipid in a relative amount of up to 200% (w/w), indicates the flexibility of the components which readily can be adapted to a composition for suitable dosage forms to be delivered to different types of patients.

The following examples show the bioavailability and the absorption of a composition according to the invention containing Fragmin® and defined monoglycerides. The compositions have been administered rectally and intraduodenally to rabbits in-vivo. The examples are not intended to limit the scope of invention, only to illustrate a special embodiment according to the invention. Example 1 shows the constituents of the defined monoglyceride used in the following examples. Example 2 shows intraduodenal and rectal absorption, respectively for a Fragmin® and the monoglyceride composition according to Example 1. Example 3 is a comparative example showing the bioavailability of intraduodenally or rectally applied Fragmin® without the monoglycerides.

The results show unambiguously that Fragmin® in this application has an absorption which result in a plasma level at least comparable to e.g. subcutaneous administration. It is surprising that no other penetration enhancer or enhancers including surface active agents or other components are necessary to achieve a favourable bioavailability and absorption. Furthermore, it is surprising that the monoglyceride is so effective, even in low concentrations, which indicate unique opportunities for new administration forms and/or routes and possibly also a specific synergistic interaction between the involved components and cellular constituents.

EXAMPLE 1

The monoglyceride used in the following examples was a highly purified fraction supplied by Karlshamns LipidTeknik AB, Sweden with the following composition:

| 8:0 caprylate | 78.4 |
|---|---|
| 10:0 caprate | 21.2 |

| | |
|---|---|
| 12:0 laurate | 0.2 |
| minors | 0.2 |
| Total | 100 |

EXAMPLE 2

The animal model

Male New Zealand white rabbits, weighing 2.5 kg to 3.5 kg were used in all experiments. After fasting for 12 hours, each animal was sedated with an intramuscular injection of Hypnorm 0.1 ml/kg (Janssen Pharmaceuticals, Belgium) and a subcutaneous injection of Atropine 0.5 ml/kg (Pharmacia, Sweden). The rabbits were anaesthetized with Mebumal 20 mg/m. The anaesthesia was subsequently maintained when needed. The animals were shaved and a medical laparotomy were performed. The test compound was then injected directly into the duodenum and the peritoneal cavity was thereafter closed. The dose was checked by weighing the syringe before and after administration of the test compound. Blood samples of 1.5 ml were collected after 0.0, 0.25, 0.5, 1.0, 1.5, 2.0, 2.5, 3.0, 3.5, 4.0, 5.0, 6.0, 7.0, 8.0, 9.0 and 10.0 hours from a catheter positioned in the ear artery. The samples were mixed with sodium citrate to a final concentration of 0.04M. The sample tubes were kept on ice until they were subjected to a centrifugation procedure (3500 rpm for 5 minutes). The anti-FXa activity in plasma was determined by an initial rate assay using bovine FXa (Pharmacia) and the chromogenic substrate S-2222. This animal model was utilized in the following experiments with intraduodenally and rectally applied Fragmin® and monoglycerides.

Intraduodenal absorption of Fragmin® and glycerides

The bioavailability of Fragmin® after an intraduodenal administration is expressed as a fraction of the area under the anti-FXa activity curve i.e. (AUC id) and (AUC sc), the latter determined to be 5.14±0.34 arbitrary units in 6 rabbits receiving a subcutaneous injection of Fragmin at a dose of 2 mg/kg. The intraduodenal absorption of Fragmin® mixed with monoglycerides according to Example 1 was tested in 5 rabbits. Fragmin® powder was dissolved in physiological saline to a final concentration of 50 mg/ml (5.0%). Four parts per weight of this Fragmin® solution were mixed with one part (weight) of monoglyceride, approximately 15 hours prior to the experiment. All rabbits received the following doses: Fragmin 25 mg/kg, monoglyceride 0.125 g/kg and saline 0.5 ml/kg. All rabbits in this experiment had detectable levels of anti-FXa activity in plasma. The maximal plasma concentration ($C_{max}$) was reached within 0.5–3.0 hours and ranged between 3.30 IU/ml and 4.70 IU/ml. The average absorption was 25.0±9.0% of subcutaneous injection.

Rectal absorption of Fragmin® glycerides

The rectal absorption of Fragmin® mixed with the highly purified monoglyceride according to Example 1, essentially composed of 8:0 caprylate and 10:0 caprate, was tested in five rabbits. The Fragmin®, manufactured by Pharmacia AB, was dissolved in physiological saline to a final concentration of 10 mg/ml. This solution was mixed with fie monoglyceride (final concentration 250 mg/ml) by vigorous shaking until fie dispersion appeared homogeneous. The Fragmin®/monoglyceride composition was injected directly into the rectum at a volume of 0.5–0.6 ml depending on the weight of fie rabbit. This corresponds to a dose of 2 mg/kg and 50 mg/kg for Fragmin® and the monoglyceride, respectively. All rabbits showed high levels of anti-FXa activity in plasma. $C_{max}$ was reached within 1.5–2 hours and ranged between 1.85 IU/ml to 2.56 IU/ml. The area under the curve (AUC) was 6.56±1.54 which is 1.3 times higher than the AUC after a subcutaneous injection. This indicates that rectal absorption of Fragmin® is similar or slightly higher than the bioavailability after a subcutaneous administration.

EXAMPLE 3

Bioavailability of Fragmin® in the absence of glycerides

The bioavailability of Fragmin® after an intraduodenal administration in the absence of the monoglycerides of Examples 1–2 was tested in 4 rabbits. Two of the rabbits received Fragmin®, 25 mg/kg, as a powder included in a gelatine capsule which was placed in the duodenum at the pylorus level The remaining two rabbits received Fragmin® dissolved in physiological saline, which was injected directly into the duodenum (total dosage 25 mg/kg). No anti-FXa activity could be detected in any of these animals over an observation period of 8–10 hours. The bioavailability of Fragmin® after a rectal administration was tested in 3 rabbits. Fragmin® was dissolved in physiological saline and injected directly into the rectum at a dosage of 10 mg/kg. Two of these rabbits had no detectable anti-FXa activity in plasma but one showed an activity of 0.2 IU/ml for 45 minutes which corresponds to a bioavailability of less than 1%. The conclusion is that the bioavailability of Fragmin® in the absence of the monoglyceride is less than 1% after an intraduodenal or a rectal administration.

I claim:

1. A homogenous composition comprising:
   (i) a therapeutically effective amount of at least one compound selected from the group consisting of heparin, heparin fragments and their derivatives, and
   (ii) as the absorption enhancer, a monoglyceride having acyl consisting essentially of a mixture of the fatty acids 8:0 caprylate and 10:0 caprate.

2. A composition according to claim 1 further comprising at least one additional physiologically acceptable additive, suitable for oral, rectal, buccal, nasal, sublingual, subcutaneous or transdermal administration.

3. A composition according to claim 2 wherein said additive is a diluent, carrier or both.

4. A composition according to claim 1 wherein said at least one compound comprises low molecular weight heparin fragments or their derivatives, or both, with a mean molecular mass of about 1000 to 10000 Dalton.

5. Oral preparation comprising a composition according to claim 1 optionally provided with release controlling membrane.

6. Buccal preparation comprising a composition according to claim 1.

7. A preparation for administration through mucous membranes comprising the composition according to claim 1.

8. Method for manufacturing the composition according to claim 1, which comprises mixing a powder and an aqueous solution or suspension of the heparin or the heparin fragment or derivative with said monoglyceride to form a homogenous composition.

9. A composition according to claim 2 wherein said at least one compound comprises low molecular weight heparin fragments or their derivatives, or both, with a mean molecular mass of about 1000 to 10000 Dalton.

10. A composition according to claim 3 wherein said at least one compound comprises low molecular weight heparin fragments or their derivatives, or both, with a mean molecular mass of about 1000 to 10000 Dalton.

11. Oral preparation comprising a composition according to claim 2 optionally provided with release controlling membrane.

12. Oral preparation comprising a composition according to claim 3 optionally provided with release controlling membrane.

13. Oral preparation comprising a composition according to claim 4 optionally provided with release controlling membrane.

14. Buccal preparation comprising a composition according to claim 2.

15. Buccal preparation comprising a composition according to claim 3.

16. Buccal preparation comprising a composition according to claim 4.

17. A preparation for administration through mucous membranes comprising the composition according to claim 3.

18. A preparation for administration through mucous membranes comprising the composition according to claim 4.

19. Method for manufacturing the composition according to claim 3, which comprises mixing a powder and an aqueous solution or suspension of the heparin or the heparin fragment or derivative with said monoglyceride to form a homogenous composition.

20. Method for manufacturing the composition according to claim 4 which comprises mixing a powder and an aqueous solution or suspension of the heparin or the heparin fragment or derivative with said monoglyceride to form a homogenous composition.

* * * * *

UNITED STATES PATENT AND TRADEMARK OFFICE
CERTIFICATE OF CORRECTION

PATENT NO. : 5,714,477
DATED : February 3, 1998
INVENTOR(S): Monica Einarsson

It is certified that error appears in the above-identified patent and that said Letters Patent is hereby corrected as shown below:

```
Title page, item [75], Inventor: should read --Monica
Einarsson, Uppsala, Sweden--.
```

Signed and Sealed this

Twenty-first Day of April, 1998

Attest:

BRUCE LEHMAN

Attesting Officer

Commissioner of Patents and Trademarks